(12) United States Patent
Procter et al.

(10) Patent No.: US 8,882,740 B2
(45) Date of Patent: Nov. 11, 2014

(54) METHOD OF DELIVERING A BIPHOSPHONATE AND/OR STRONTIUM RANELATE BELOW THE SURFACE OF A BONE

(75) Inventors: Philip Procter, Geneva (CH); Anders Jönsson, Onsala (SE); Jörg Arnoldi, Bettlach (CH)

(73) Assignee: Stryker Trauma GmbH (DE)

( * ) Notice: Subject to any disclaimer, the term of this patent is extended or adjusted under 35 U.S.C. 154(b) by 691 days.

(21) Appl. No.: 12/975,639

(22) Filed: Dec. 22, 2010

(65) Prior Publication Data

US 2011/0172632 A1    Jul. 14, 2011

Related U.S. Application Data

(60) Provisional application No. 61/289,666, filed on Dec. 23, 2009.

(51) Int. Cl.
*A61M 31/00* (2006.01)
*A61L 24/02* (2006.01)
*A61L 24/00* (2006.01)
*A61B 17/92* (2006.01)
*A61B 17/86* (2006.01)

(52) U.S. Cl.
CPC .......... *A61L 24/0042* (2013.01); *A61L 2400/06* (2013.01); *A61B 2017/922* (2013.01); *A61B 17/86* (2013.01); *A61L 24/02* (2013.01); *A61L 2430/02* (2013.01)
USPC ............................................ 604/500; 606/92

(58) Field of Classification Search
CPC ....................................................... A61L 24/02
USPC .................................. 604/500; 606/92, 86 R
See application file for complete search history.

(56) References Cited

U.S. PATENT DOCUMENTS

| 4,753,652 A | 6/1988 | Langer et al. |
| 4,761,406 A | 8/1988 | Flora et al. |
| 4,777,163 A | 10/1988 | Bosies et al. |
| 4,939,130 A | 7/1990 | Jaeggi et al. |

(Continued)

FOREIGN PATENT DOCUMENTS

| CN | 1524864 A | 9/2004 |
| CN | 1693308 A | 11/2005 |

(Continued)

OTHER PUBLICATIONS

Aspenberg, P., Bisphosphonates and implants: An overview, Acta Orthopaedica, 80 (1):119-123 (2009).

(Continued)

*Primary Examiner* — Edelmira Bosques
(74) *Attorney, Agent, or Firm* — Lerner, David, Littenberg, Krumholz & Mentlik, LLP

(57) ABSTRACT

A method for delivering a bisphosphonate and/or strontium ranelate below the surface of a bone using a mechanical force. The method includes the steps of combining a bisphosphonate and/or strontium ranelate with a carrier to form a delivery composition and delivering an effective amount of the delivery composition below the surface of the bone with a mechanical force. Also provided is a method for strengthening a portion of a bone. This method includes the step of delivering an effective amount of a bisphosphonate and/or strontium ranelate below the surface of a portion of a bone with a mechanical force.

19 Claims, 10 Drawing Sheets

Surgical Technique

(56) References Cited

U.S. PATENT DOCUMENTS

| | | |
|---|---|---|
| 5,196,409 A | 3/1993 | Breuer et al. |
| 5,270,365 A | 12/1993 | Gertz et al. |
| 5,403,829 A | 4/1995 | Lehtinen et al. |
| 5,488,041 A | 1/1996 | Barbier et al. |
| 5,616,560 A | 4/1997 | Geddes et al. |
| 5,646,134 A | 7/1997 | Yates |
| 5,733,564 A | 3/1998 | Lehtinen |
| 5,876,454 A | 3/1999 | Nanci et al. |
| 5,891,863 A | 4/1999 | Yates |
| 5,934,287 A * | 8/1999 | Hayashi et al. .............. 128/898 |
| 5,965,547 A | 10/1999 | Goodship et al. |
| 5,972,913 A | 10/1999 | Yates |
| 5,994,329 A | 11/1999 | Daifotis et al. |
| 6,015,801 A | 1/2000 | Daifotis et al. |
| 6,225,294 B1 | 5/2001 | Daifotis et al. |
| 6,333,316 B1 | 12/2001 | Daifotis et al. |
| 6,410,782 B1 | 6/2002 | VanGulik et al. |
| 6,432,931 B1 | 8/2002 | Reszka et al. |
| 6,432,932 B1 | 8/2002 | Daifotis et al. |
| 6,465,443 B2 | 10/2002 | Daifotis et al. |
| 6,544,967 B2 | 4/2003 | Daifotis et al. |
| 6,596,338 B2 | 7/2003 | Scott et al. |
| 6,692,758 B1 | 2/2004 | Ito et al. |
| 6,699,850 B2 | 3/2004 | Reszka et al. |
| 6,828,312 B2 | 12/2004 | Jiao et al. |
| 7,090,496 B2 | 8/2006 | Descouts et al. |
| 7,163,690 B2 | 1/2007 | Aspenberg et al. |
| 2002/0151876 A1 | 10/2002 | Chan |
| 2003/0003128 A1* | 1/2003 | Chiarelli ..................... 424/423 |
| 2004/0023048 A1 | 2/2004 | Schwartz et al. |
| 2004/0147484 A1 | 7/2004 | Boyd et al. |
| 2004/0157798 A1* | 8/2004 | Little ............................ 514/89 |
| 2004/0158329 A1 | 8/2004 | Link |
| 2004/0230076 A1 | 11/2004 | Lifshitz-Liron et al. |
| 2005/0031704 A1 | 2/2005 | Ahn |
| 2005/0054616 A1 | 3/2005 | Aronhime et al. |
| 2005/0079200 A1 | 4/2005 | Rathenow et al. |
| 2005/0079201 A1 | 4/2005 | Rathenow et al. |
| 2005/0095267 A1 | 5/2005 | Campbell et al. |
| 2005/0119230 A1 | 6/2005 | Glausch et al. |
| 2005/0196425 A1 | 9/2005 | Zamora et al. |
| 2005/0246033 A1 | 11/2005 | Link |
| 2005/0288509 A1 | 12/2005 | De Ferra et al. |
| 2006/0115514 A1 | 6/2006 | Gengrinovitch |
| 2006/0128960 A1 | 6/2006 | Lidor-Hadas et al. |
| 2006/0177494 A1 | 8/2006 | Cormier et al. |
| 2006/0178439 A1 | 8/2006 | Mohakhud et al. |
| 2006/0188542 A1 | 8/2006 | Bobyn et al. |
| 2006/0229715 A1 | 10/2006 | Istephanous et al. |
| 2006/0258625 A1 | 11/2006 | Deshpande et al. |
| 2006/0270645 A1 | 11/2006 | Parhami |
| 2006/0275340 A1 | 12/2006 | Udipi et al. |
| 2006/0293524 A1 | 12/2006 | Patel et al. |
| 2007/0015736 A1 | 1/2007 | Glausch et al. |
| 2007/0066569 A1 | 3/2007 | Senthilkumar et al. |
| 2007/0066571 A1 | 3/2007 | Stockel et al. |
| 2007/0088161 A1 | 4/2007 | Stockel et al. |
| 2007/0088442 A1 | 4/2007 | Cima et al. |
| 2007/0112197 A1 | 5/2007 | Grassi et al. |
| 2009/0319044 A1* | 12/2009 | Lee ............................ 623/16.11 |

FOREIGN PATENT DOCUMENTS

| | | |
|---|---|---|
| EP | 0094714 A2 | 11/1983 |
| WO | 9400129 A1 | 1/1994 |
| WO | 9414455 A1 | 7/1994 |
| WO | 9421266 A1 | 9/1994 |
| WO | 9423770 A1 | 10/1994 |
| WO | 9530421 A1 | 11/1995 |
| WO | 9639107 A1 | 12/1996 |
| WO | 0000177 A1 | 1/2000 |
| WO | 0017214 A1 | 3/2000 |
| WO | 0113922 A1 | 3/2001 |
| WO | 0204038 A1 | 1/2002 |
| WO | 0211704 A2 | 2/2002 |
| WO | 02098307 A1 | 12/2002 |
| WO | 2005009496 A1 | 2/2005 |
| WO | 2005061617 A1 | 7/2005 |
| WO | 2005063717 A1 | 7/2005 |
| WO | 2005066188 A1 | 7/2005 |
| WO | 2005087284 A1 | 9/2005 |
| WO | 2006007730 A1 | 1/2006 |
| WO | 2006097932 A2 | 9/2006 |
| WO | 2006134603 A1 | 12/2006 |
| WO | 2007016982 A1 | 2/2007 |
| WO | 2007023342 A2 | 3/2007 |
| WO | 2007024493 A1 | 3/2007 |
| WO | 2007032808 A1 | 3/2007 |
| WO | 2007048263 A2 | 5/2007 |

OTHER PUBLICATIONS

Tengvall P, et al., Surface immobilized bisphosphonate improves stainless-steel screw fixation in rats, Biomateri•als 25 (11): 2133-8 (2004).

V. A. Stadelmann, et al., Implants delivering bisphosphonate locally increase periprosthetic bone density in and osteoporotic sheep model. A pilot study, European Cells and Materials, 16:10-16 (2008).

Wermelin, K., et al., Stainless steel screws coated with bisphosphonates gave stronger fixation and more surrounding bone. Histomorphometry in rats, Bone, 42:365-371 (2008).

\* cited by examiner

Surgical Technique
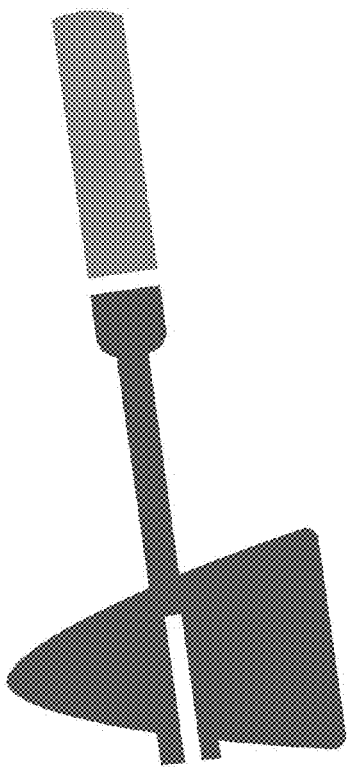
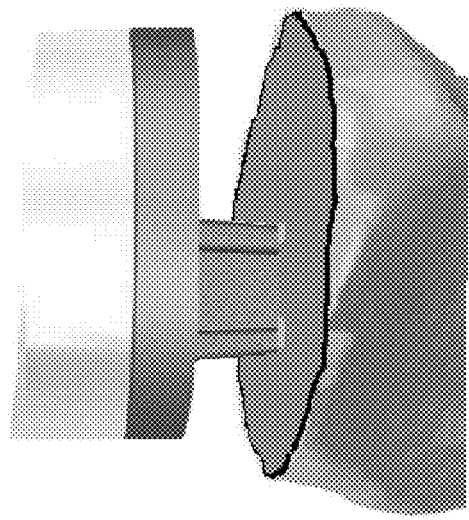
Definitve implant inserted
Figure 4

METHOD OF DELIVERING A BIPHOSPHONATE AND/OR STRONTIUM RANELATE BELOW THE SURFACE OF A BONE

CROSS-REFERENCE TO RELATED APPLICATION

This application claims the benefit of the filing date of U.S. Provisional Patent Application No. 61/289,666 filed Dec. 23, 2009, the disclosure of which is hereby incorporated herein by reference.

BACKGROUND OF THE INVENTION

The present invention relates to a method of delivering a bisphosphonate and/or strontium ranelate below the surface of a bone using a mechanical force.

Loss of bone strength near the site of a bone implant or prosthesis is a major factor leading to the eventual failure of such implants and prosthesis. These failures result not only in discomfort for the patients, but often the need for follow-up surgery to replace the failing implant or prosthetic.

Living bone is in constant turnover. Existing bone undergoes resorption and new bone is deposited. In healthy bone, the deposition of new bone matches or exceeds resorption of existing bone. However, when this balance is lost, e.g., due to disease, nutritional deficiency, or tissue damage, the resorption of bone exceeds the deposition of bone and a net loss of bone results.

The loss of bone produces weakening of the bones, as seen in osteoporosis. Such bone loss is common near the site of bone implants and prosthetics. The loss of bone adjacent to an implant or prosthetic contributes to the weakening of the attachment, and eventual failure, of the implant or prosthetic.

The most common treatment for bone loss is the administration of a bisphosphonate. Bisphosphonates preferentially kill or inactivate osteoclast cells. Osteoclast cells break down bone tissue. Conversely, osteoblast cells form bone tissue. Thus, bisphosphonate administration reduces bone resorption without effecting bone formation, in some instances leading to a net increase of bone mass over an untreated state. Bisphosphonates can also be administered with other actives, such as for example, vitamin D.

Systemic administration of bisphosphonates, e.g., orally or intravenously, can lead to side effects. Oral administration can result in upset stomach and severe inflammation and erosion of the esophagus. Administration is also very cumbersome and inconvenient. Intravenous administration can produce fever and flu-like symptoms and, in high doses, has been associated with osteonecrosis of the jaw. Severe bone, muscle, and joint pain have also been reported after systemic bisphosphonate treatment.

In patients who are intolerant or otherwise contraindicated for bisphosphonate treatment systemically, or as a supplement to traditional bisphosphonate treatment, local delivery of a bisphosphonate in conjunction with an implant or prosthesis is an attractive alternative. A number of methods for local delivery of a bisphosphonate have been proposed.

For example, the combination of a bisphosphonate with an apatite coating on an implant that is commonly used in orthopedic implants has been shown (V. A. Stadelmann, et al., *Implants delivering bisphosphonate locally increase periprosthetic bone density in and osteoporotic sheep model. A pilot study*, European Cells and Materials, 16:10-16 (2008)). Bisphosphonates, however, bind preferentially to calcium salts and their range of influence is limited to a region very close to the bone implant interface, i.e., from 0 to 0.5 millimeters below the surface of the bone. Fibrinogen can be used to bind a bisphosphonate to an implant (Tengvall P, et al., *Surface immobilized bisphosphonate improves stainless-steel screw fixation in rats*, Biomaterials 25(11): 2133-8 (2004); Aspenberg, P., Bisphosphonates and implants: An overview, *Acta Orthopaedica*, 80 (1):119-123 (2009)), but the depth of penetration of the bisphosphonate is similarly limited. A bisphosphonate can also be delivered either by painting it onto the bone, or in combination with bone chips. The disadvantage in such cases is that it is impossible to determine where the drug is delivered or the amount delivered to the bone, because the distribution of the drug is impossible to control in either case.

Strontium ranelate is an antiosteoporoitic compound known to both reduce resorption of bone by the osteoclasts and increase bone deposition by osteoblasts. Thus, strontium ranelate produces a rebalancing to bone turnover in favor of formation of bones.

SUMMARY OF THE INVENTION

The present invention is a method of delivering a bisphosphonate and/or strontium ranelate using a carrier that, in combination with appropriate instrumentation, enables delivery of the bisphosphonate and/or strontium ranelate to a greater range of depth below the surface of cancellous bone than is currently possible using known methods. Because the bisphosphonate and/or strontium ranelate is inserted to a much greater depth below the surface of the cancellous bone, its influence is over a larger bone volume, and thus, the beneficial effect in reducing bone resorption by osteoclasts, and in the case of strontium ranelate increasing bone deposition by osteoblasts, is much greater.

One embodiment of the present invention is a method for delivering a bisphosphonate and/or strontium ranelate below a surface of a bone using a mechanical force. This method includes the steps of combining a bisphosphonate and/or strontium ranelate with a carrier to form a delivery composition and delivering an effective amount of the delivery composition below the surface of the bone with a mechanical force.

Another embodiment of the present invention is a method for strengthening a portion of a bone. This method includes the step of delivering an effective amount of a bisphosphonate and/or strontium ranelate below a surface of a portion of a bone with a mechanical force.

BRIEF DESCRIPTION OF THE DRAWINGS

The present invention will be better understood on reading the following detailed description of non-limiting embodiments thereof, and on examining the accompanying drawings, in which:

FIGS. 1-5 are sequential views exemplifying a method of the present invention in conjunction with a knee implant;

DETAILED DESCRIPTION

Figure 1:
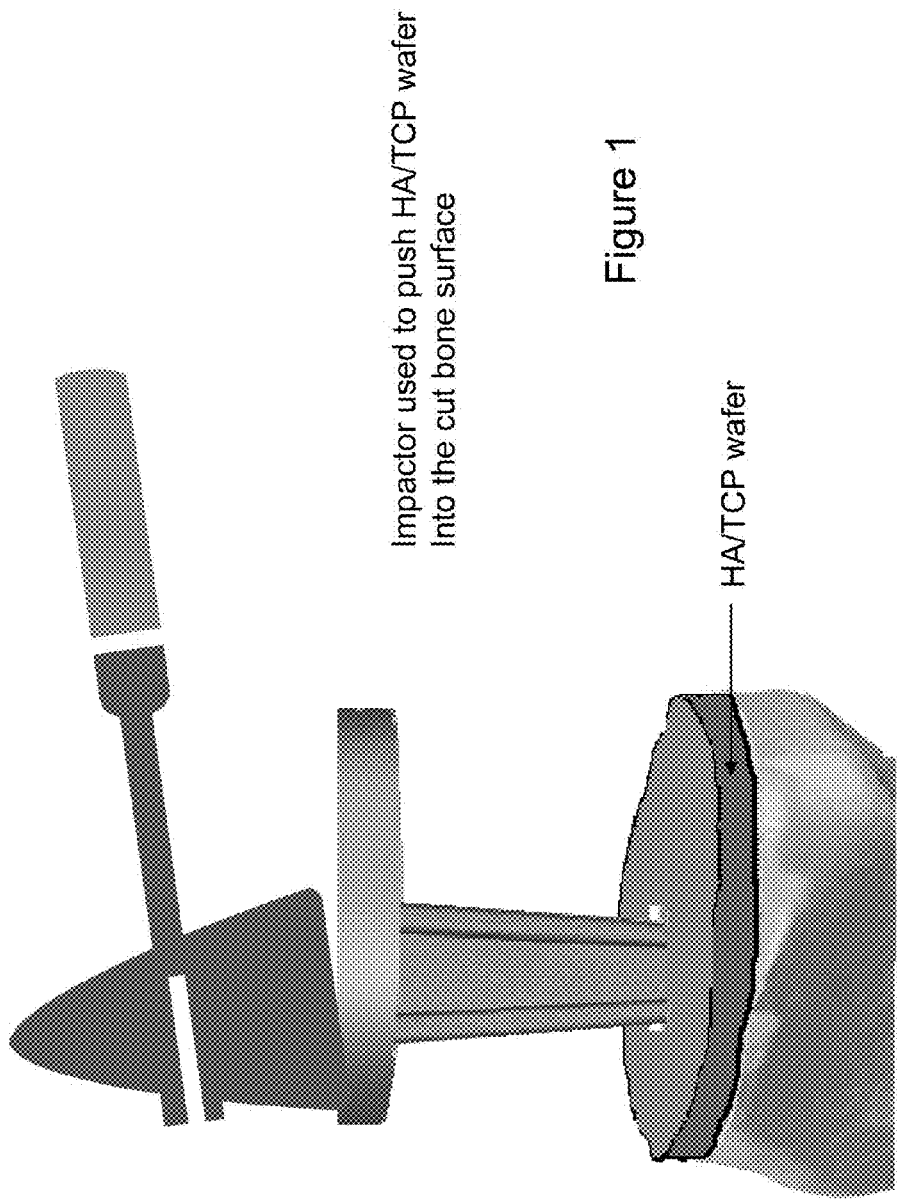

One embodiment of the present invention is a method for delivering a bisphosphonate and/or strontium ranelate below a surface of a bone. This method includes combining the bisphosphonate and/or strontium ranelate with a carrier to form a delivery composition and delivering an effective amount of the delivery composition below the surface of the bone with a mechanical force.

Bisphosphonates have the following structure (shown deprotonated):

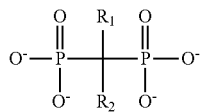

Common bisphosphonates are shown in Table 1:

TABLE 1

Common bisphosphonates.

| BISPHOSPHONATE | $R_1$ | $R_2$ |
|---|---|---|
| Alendronate | —OH | —$(CH_2)_3$—$NH_2$ |
| Clodronate | —Cl | —Cl |
| Etidronate | —OH | —$CH_3$ |
| Ibandronate | —OH | ![structure] |
| Neridronate | —OH | —$(CH_2)_5$—$NH_2$ |
| Olpadronate | —OH | —$(CH_2)_2N(CH_3)_2$ |
| Pamidronate | —OH | —$CH_2$—$CH_2$—$NH_2$ |
| Risedronate | —OH | ![structure] |
| Tiludronate | —H | ![structure] |
| Zoledronate | —OH | ![structure] |

Preferably, the bisphosphonate is alendronate, clodronate, etidronate, ibandronate, neridronate, olpadronate, pamidronate, risedronate, tiludronate, or zoledronate. More preferably, the bisphosphonate is zoledronate.

Strontium ranelate has the following structure:

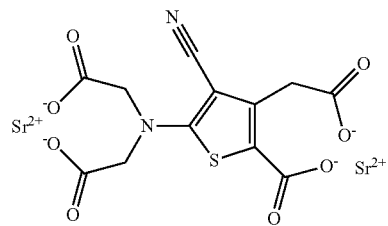

In embodiments of the present invention, a bisphosphonate is delivered without strontium ranelate below a surface of a bone. In other embodiments strontium ranelate is delivered without any bisphosphonate below a surface of a bone. In yet other embodiments, a bisphosphonate and strontium ranelate are both delivered below a surface of a bone.

As used herein, the term "effective amount" means the amount of a compound or composition sufficient to produce a desired effect in a tissue or structure to which the compound or composition is delivered. Preferably, an effective amount of a delivery composition or a bisphosphonate and/or strontium ranelate is an amount sufficient to strengthen a bone at and adjacent to the site of administration. In an embodiment of the present invention, the bisphosphonate and/or strontium ranelate is provided in an amount of about 0.1 to about 100 micrograms per square centimeter of bone surface. As used herein, the term "to strengthen bone" or "strengthening bone" means to cause at least a portion of a bone to undergo decreased resorption of bone, increased deposition of bone, or both, as compared to the untreated state.

As used herein, the term "delivery composition" means a composition comprising a bisphosphonate and/or strontium ranelate and at least one carrier. As used herein, the term "carrier" means a substance suitable to be delivered below the surface of a bone using a mechanical force. Preferably, the carrier is a resorbable substance, such as polylactic acid (PLA) or poly-L/D-lactide (PLDLA), a gel, such as a hydrogel, or hyaluronic acid; or a hydoxyapatite or tricalcium phosphate in any form, e.g., pastes, gels, granules, blocks, and wedges. More preferably the carrier is a bone graft material or a bone cement.

As used herein, the term "bone graft material" means a solid substance used to replace missing or damaged bone or augment or strengthen existing bone. Examples of bone graft materials useful in the present invention are autologous bone, allograft bone, and synthetic bone substitutes. Bone graft materials may be provided in any useful form, including for example, injectable gels, pastes, granules, bocks, and wedges. Preferably, the bone graft material is a synthetic bone substitute. Preferably, the synthetic bone substitute comprises tricalcium phosphate or hydroxylapatite. In embodiments, the synthetic bone substitute comprises tricalcium phosphate and hydroxylapatite. In other embodiments, the synthetic bone substitute comprises a combination of a polymer and a mineral. Such combinations include polylactic acid (or a derivative thereof) combined with one or more of hydroxylapatite, tricalcium phosphate, and calcium sulphate. An example of a synthetic bone graft material is BoneSave™

(STRYKER Corp., Kalamazoo, Mich.), a biocompatible matrix containing 80% tricalcium phosphate and 20% hydroxyapatite The bone graft material used in the present invention has physical and mechanical properties that make it possible to deliver the bone graft material below the surface of the bone using a mechanical force. Preferably, the bone graft material is in the form of a solid, particles, or an aggregation of particles.

A bisphosphonate and/or strontium ranelate may be combined with the bone graft material at any stage during the production and use of the bone graft material. Preferably, the bisphosphonate and/or strontium ranelate is coated on the surface of a particle or coated on the surface of a solid form or aggregation of particles of the bone graft material. The bisphosphonate and/or strontium ranelate may be introduced into the bone graft material during its manufacture, to ensure that the correct dose is administered upon use in the patient. In an embodiment of the present invention, the bisphosphonate and/or strontium ranelate is added as a powder at the time of manufacture of the bone graft material. In another embodiment of the present invention, the bisphosphonate and/or strontium ranelate is added in the form of a liquid that can soak into and penetrate the pores of the bone graft material at the time of manufacture.

Preferably, the solid form or aggregate of particles has a shape adapted to allow it to be seated or placed into a recess or other surface feature of the bone to allow for accurate placement and delivery of the bisphosphonate to a desired treatment site, e.g., at the site of an implant or prosthesis. More preferably, the solid form or aggregate of particles is in the shape of a cylinder adapted to be placed in a recess created to securely receive a screw or other fastening device or in the shape of a wafer of a shape and size adapted to be impacted below the surface of a bone prepared for receiving an implant or prosthesis.

Preferably, when a delivery composition containing the bone graft material and a bisphosphonate and/or strontium ranelate is impacted by an impact device the delivery composition is crushed or broken into particles, if not already in particulate form, and driven below the surface of the bone. Also preferably, the delivery composition is crushed or broken into particles, if not already in particulate form, and driven below the surface of the bone when a screw is inserted and seated in recess created for securely receiving the screw, wherein the recess is filled, at least in part, with the delivery composition prior to insertion and seating of the screw.

Preferably, the particles of the delivery composition have a mean diameter of from about 2 millimeters to about 8 millimeters, more preferably from about 4 millimeters to about 5 millimeters. In an embodiment of the present invention, the particles of the delivery composition have a hardness greater than the surrounding cancellous bone.

As used herein, the term "bone cement" means an adhesive that can be used to fill a void or affix bone, bone graft material, or an implant or prosthetic to bone. Preferably, the bone cement comprises tricalcium phosphate or hydroxylapatite. In embodiments, the bone cement comprises tricalcium phosphate and hydroxylapatite. In other embodiments, the bone cement comprises a combination of a polymer and a mineral. Such combinations include polylactic acid (or a derivative thereof) combined with one or more of hydroxylapatite, tricalcium phosphate, and calcium sulphate. An example of a bone cement useful in the present invention is HYDROSET™ (STRYKER Corp., Kalamazoo, Mich.), a self-setting calcium phosphate bone cement containing hydroxyapatite.

A bisphosphonate and/or strontium ranelate may be combined with the bone cement at any stage during the production and use of the bone cement. Preferably, the bisphosphonate and/or strontium ranelate is admixed with the bone cement during manufacture or after manufacture and prior to use. In an embodiment of the present invention, the bone cement provides about 0.1 to about 100 micrograms of bisphosphonate and/or strontium ranelate per square centimeter when applied to an implant and/or bone.

A delivery composition containing a bone cement and a bisphosphonate and/or strontium ranelate is delivered below the surface of the bone when a mechanical force is applied to the delivery composition. Preferably, the delivery composition is driven below the surface of the bone when a screw is inserted and seated in recess created to securely receive the screw, wherein the recess is filled, at least in part, with the delivery composition prior to insertion and seating of the screw.

As used herein "mechanical force" means any action that results in movement or deformation of a delivery composition when the mechanical force is applied to the delivery composition. Preferably, the mechanical force is provided by an impact device, e.g., a hammer or piston, or by the insertion of a screw into the bone.

In the present invention, the bisphosphonate and/or strontium ranelate is delivered below the surface of the bone to a maximum, depth that exceeds the depth of the penetration of a bisphosphonate and/or strontium ranelate applied merely to the surface of the bone or to the surface of an implant or prosthesis. (See e.g., Wermelin, K., et al., *Stainless steel screws coated with bisphosphonates gave stronger fixation and more surrounding bone. Histomorphometry in rats, Bone,* 42:365-371 (2008) (showing that the effect of the bisphosphonate is limited to a region close to the implant and that the influence of bisphosphonate at 0.5 mm depth is much less than at 0.25 mm depth.))

Thus, due to the high affinity of calcium for bisphosphonates, it is clear that at 1 mm depth from the implant surface there will be very little measurable effect. Therefore, pushing the drug physically to depth of 1 mm or greater, for example, would deliver the drug further into the bone.

In an embodiment of the present invention, the bisphosphonate and/or strontium ranelate is delivered to a maximum depth of at least about 1 millimeter to about 10 millimeters, in other embodiments from about 2 millimeters to about 8 millimeters, an in yet other embodiment from about 2 millimeters to about 5 millimeters. The depth of delivery can be assessed by carrying out the methods of the present invention on non-living bone or non-human bone, e.g., by simulating the methods on cadverous or animal bone.

The delivery composition may also include one or more additives. As used herein, the term "additive" means a compound or composition that provides useful or desired properties to the delivery composition. Examples of additives useful in the present invention include, for example, osteogenic factors (such as osteoplastic protein, growth hormone, or parathyroid hormone), antibiotics, hardening agents, growth factors, and materials to provide additional strength to the bone graft material or bone cement, such as fibers, mats, meshes, and woven materials.

In an embodiment of the present invention, the method of the present invention is preceded by, accompanied by, or followed by one or more additional therapies that strengthen the bone. As used herein, the term "additional therapy" means any action or treatment that decreases bone resorption or increases bone deposition over an untreated state. Preferably, the additional therapy is mechanical vibration, physical therapy, or administration of an additive, as defined above not as part of the delivery composition.

Another embodiment of the present invention is a method for strengthening a portion of a bone. This method includes the step of delivering an effective amount of a bisphosphonate and/or strontium ranelate below the surface of a portion of a bone with a mechanical force.

EXAMPLES

Example 1

In preparation for a knee implant, the tibial head is cut to form a tibial plateau adapted to receive a knee implant. A wafer is formed having a height of about 5 millimeters and a shape congruent with that of the tibial plateau. The wafer is composed of an aggregate of particles of a delivery composition containing hydroxylapatite and tricalcium phosphate. The particles are coated with a bisphosphonate and/or strontium ranelate before formation of the wafer and/or the wafer is impregnated with a bisphosphonate and/or strontium ranelate after formation.

Figure 2:
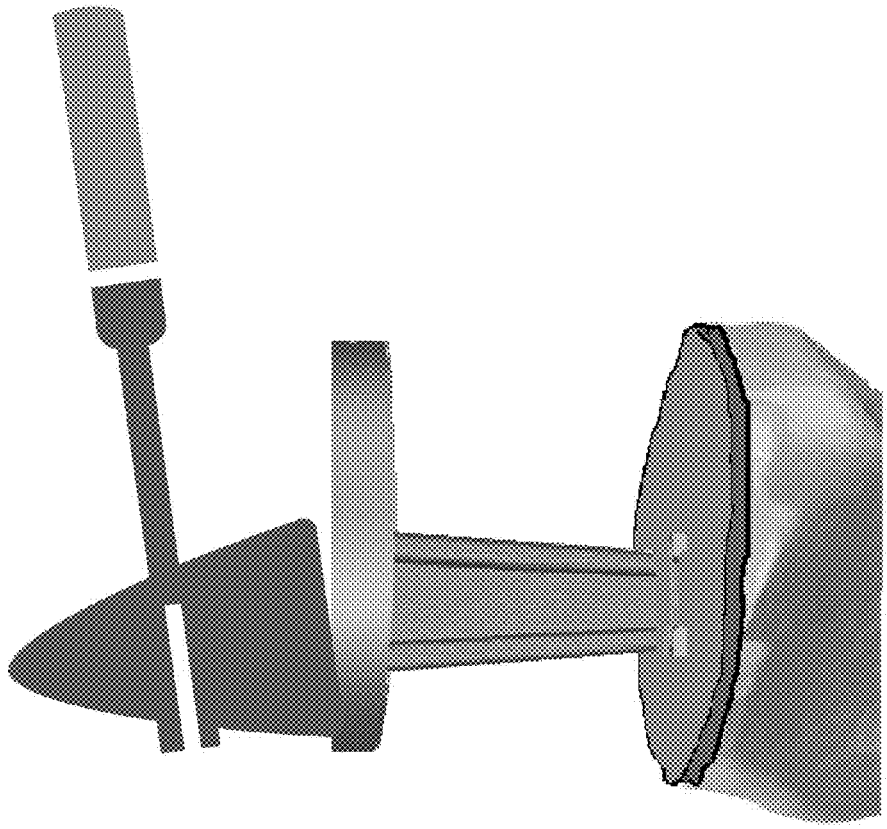
Figure 3:
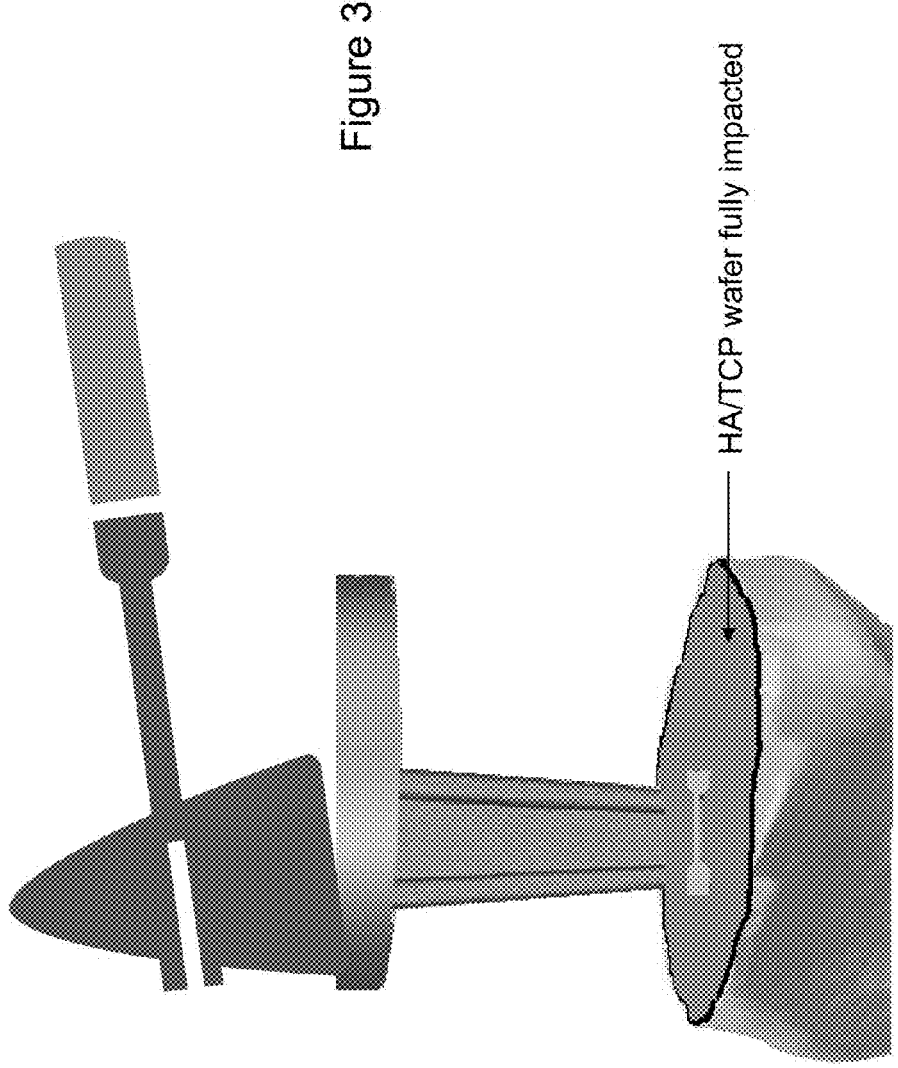
Figure 5:
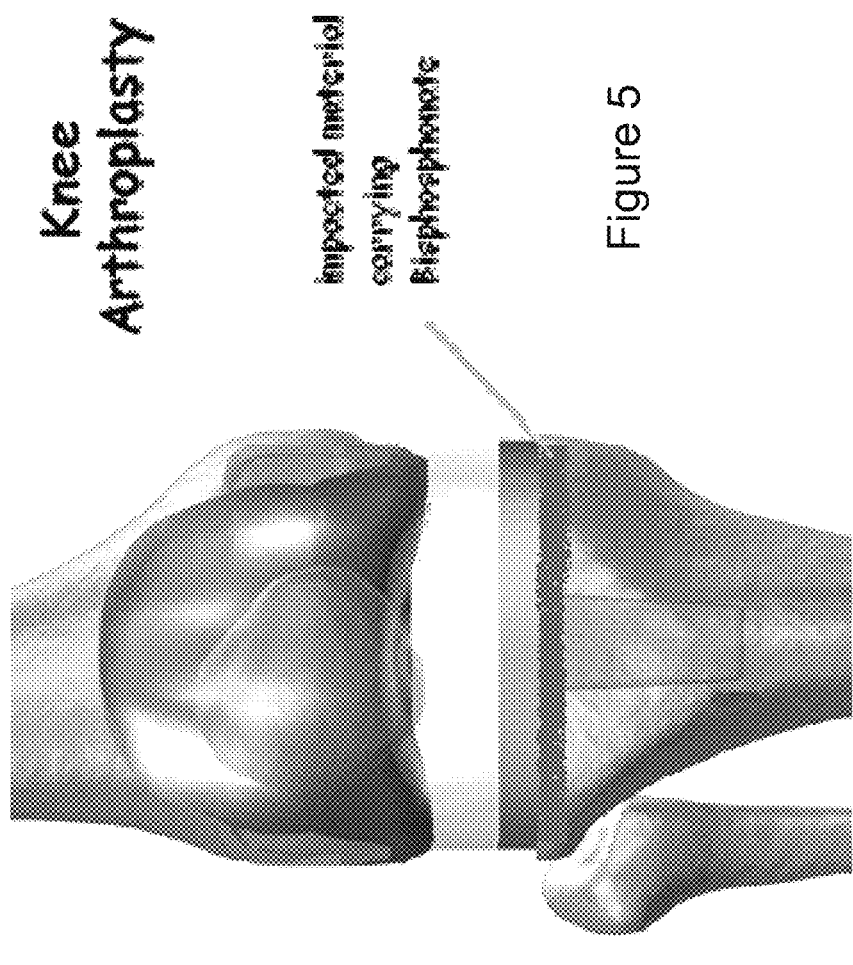

The wafer is placed atop the tibial plateau. An impactor approximately congruent with the tibial plateau is then placed atop the wafer. (FIG. 1.) A hammer is then used to strike the impactor thereby crushing the wafer into particles and delivering the particles, including the bisphosphonate and/or strontium ranelate, to a maximum depth of about 5 millimeters below the surface of the bone. (FIGS. 2-3.) A definitive knee implant is then inserted into its final position. (FIGS. 4-5.)

Example 2

Figure 6:
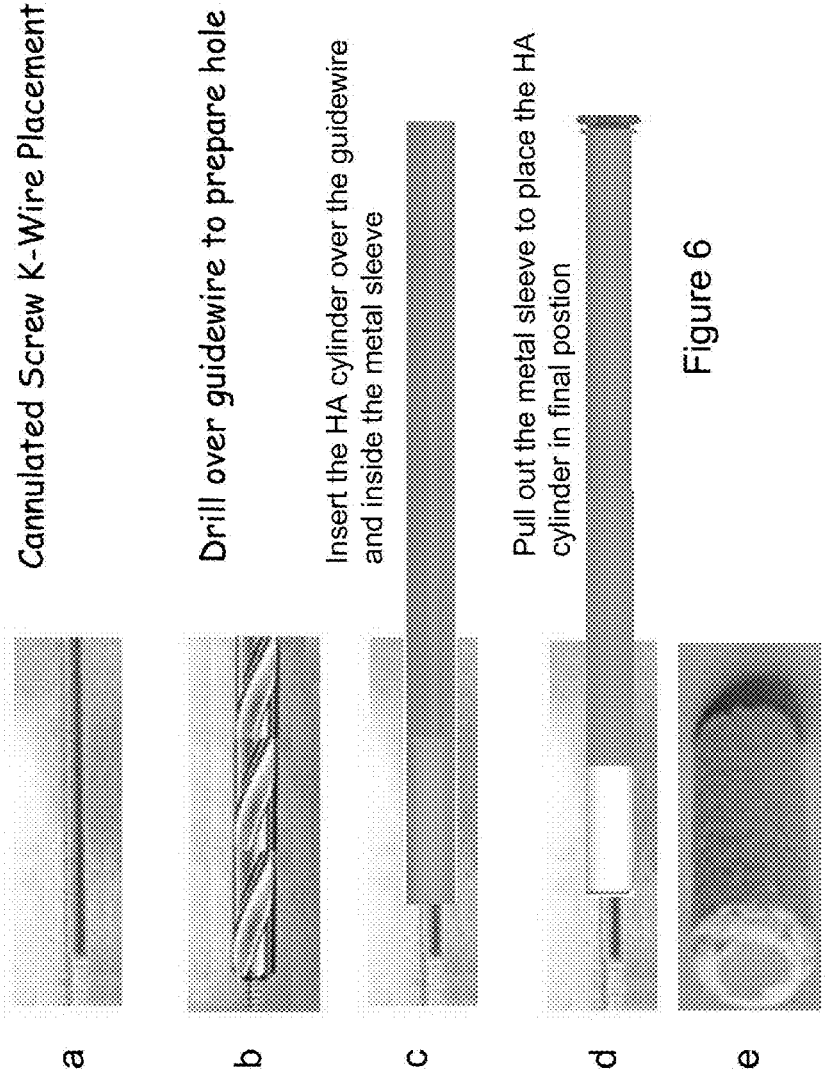
FIGS. 6a-d are drawings demonstrating the sequence for creating a recess for receiving a screw and placing a cylinder of a delivery composition containing a bisphosphonate and/or strontium ranelate and a bone graft material in the recess prior to insertion of the screw and FIG. 6e is a photograph of a cylinder of the delivery material.
Figure 7:
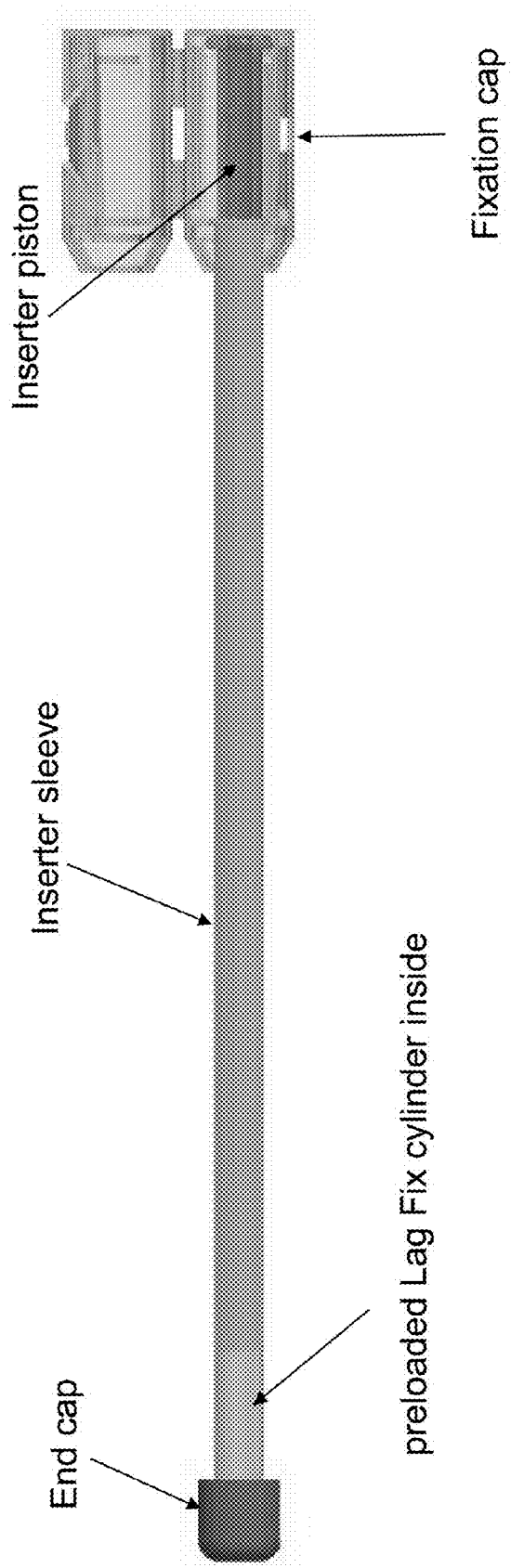
FIG. 7 is a side view of a cylinder inserter for placing a cylinder of a delivery composition containing bisphosphonate and/or strontium ranelate and a bone graft material within a recess for receiving a screw prior to insertion of the screw.
Figure 8:
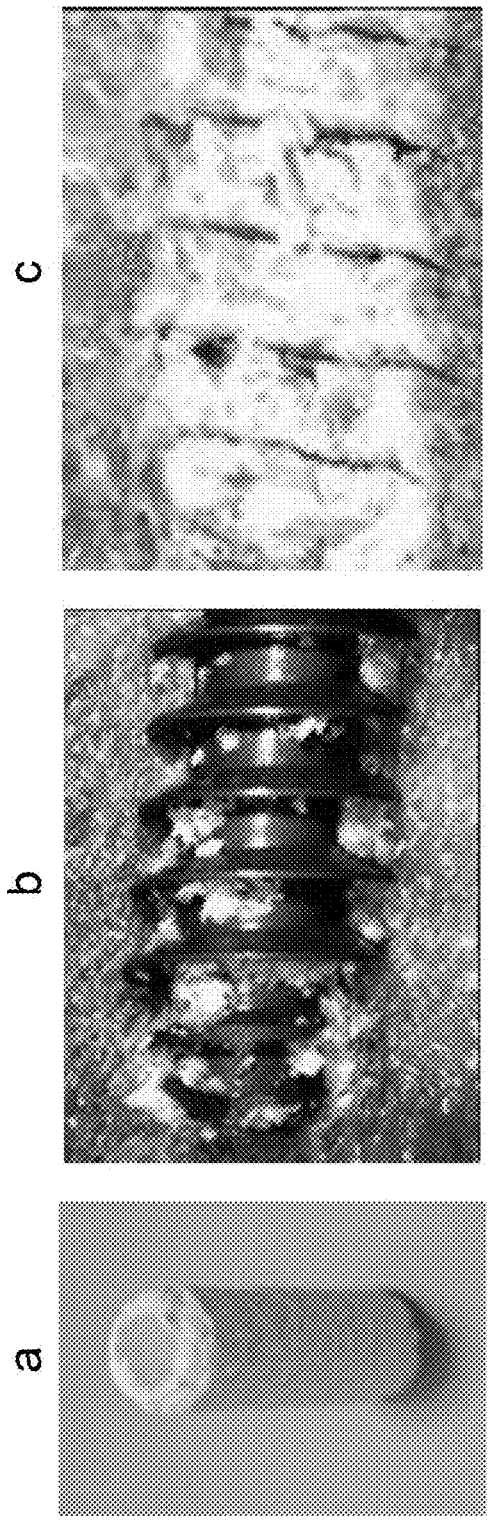
FIG. 8a is a photograph of a cylinder of a delivery composition containing bisphosphonate and a bone graft material.
FIG. 8b is a photograph of a portion of bone in which a screw has delivered the delivery composition below the surface of the bone.
FIG. 8c is a photograph of the delivery composition below the surface of the bone after removal of the screw.
Figure 9:
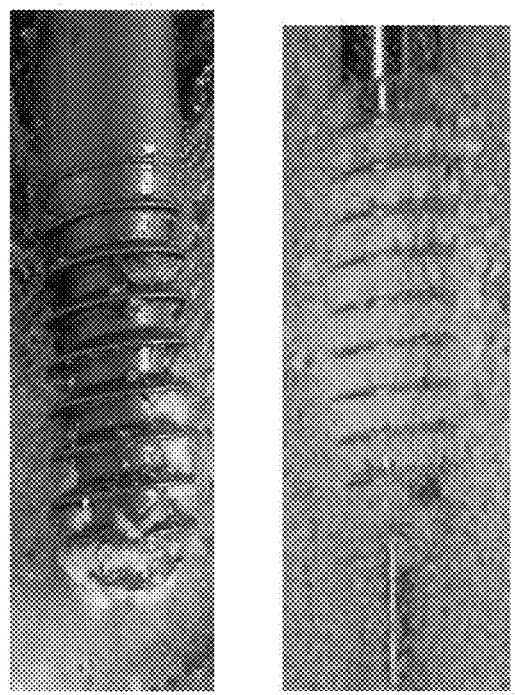
FIGS. 9a and b are photographs of the insertion of a screw into a recess in the bone containing a cylinder of a delivery composition containing a bisphosphonate and a bone graft material thereby delivering the delivery composition below the surface of the bone.

In preparation for the placement of an implant or prosthesis, a hole is prepared for receipt of a screw. A cannulated Screw K-Wire is placed into the bone at the site chosen for the screw. (FIG. 6a.) A hole is then drilled over the wire. (FIG. 6b.) An inserter sleeve of a cylinder inserter (FIG. 7.) containing within it at a first end a solid cylinder a delivery composition containing hydroxylapatite, tricalcium phosphate, and a bisphosphonate and/or strontium ranelate (FIGS. 6e and 8a) is inserted into the hole. (FIG. 6c.) The remainder of the inserter sleeve, e.g., from the proximal end of the cylinder to a second end of the inserter sleeve is filled with an inserter piston. (FIG. 7.) As the inserter piston is held without movement, the inserter sleeve is withdrawn from the hole. The inserter piston is then withdrawn leaving the solid cylinder within the hole. (FIG. 6d.)

A screw is then inserted and seated into the hole. The mechanical force applied by the insertion and seating of the screw crushes the solid cylinder into particles and pushes the particles below the surface of the surrounding bone to a maximum depth of about 2 millimeters to about 3 millimeters. (FIGS. 8b-c and 9a-b.)

Example 3

Figure 10:
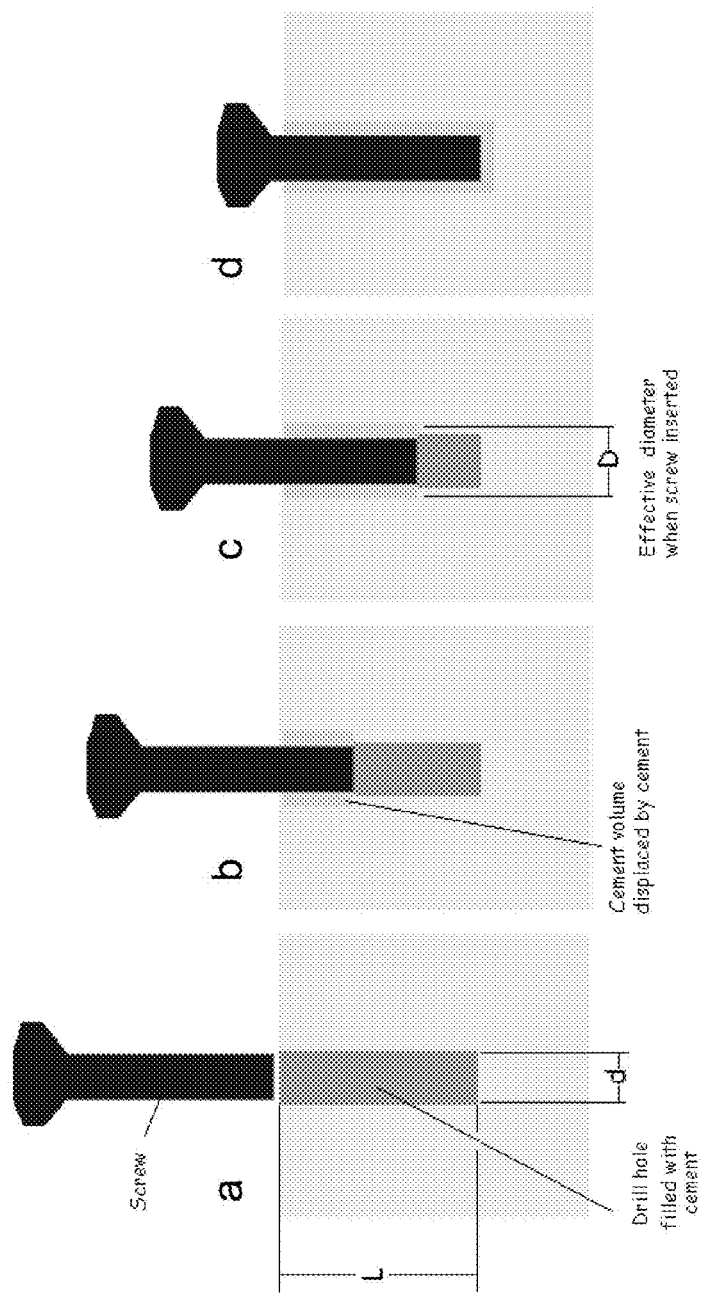
FIGS. 10a-d are drawings demonstrating the sequence for delivering a delivery composition containing a bisphosphonate and/or strontium ranelate and a bone cement below the surface of the bone by insertion of a screw into a recess in the bone that is pre-filled with the delivery composition.

In preparation for the placement of an implant or prosthesis, a hole is prepared for receipt of a screw as described in EXAMPLE 2. The hole is then filled by injection to a desired depth with a delivery composition containing a bone cement and a bisphosphonate and/or strontium ranelate. (FIG. 10a.)

A screw is then inserted and seated in the hole. The fins of the screw seal the delivery composition from the surroundings. (FIG. 10b.) As the screw is driven into its final position, the delivery composition is pushed below the surface of the surrounding bone to a maximum depth of about 2 millimeters to about 3 millimeters. (FIGS. 10c-d.)

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for delivering a bisphosphonate, strontium ranelate or both below a recess or surface feature of a bone comprising:
   a) combining the bisphosphonate, strontium ranelate or both with a carrier to form a delivery composition, wherein the delivery composition is in the form of one selected from the group consisting of a solid, particles and a aggregation of particles
   b) placing the delivery composition into the recess or surface feature of the bone
   c) placing an impact device atop the delivery composition or seating a fastening device into the recess or surface feature atop the delivery composition; and
   d) using mechanical force of the impact device or the fastening device to crush or break the delivery composition while driving an effective amount of the delivery composition about 1 mm to about 10 mm delivering an effective amount of the delivery composition below the recess or surface feature of the bone.

2. The method as set forth in claim 1, wherein the bisphosphonate is selected from the group consisting of alendronate, clodronate, etidronate, ibandronate, neridronate, olpadronate, pamidronate, risedronate, tiludronate, and zoledronate.

3. The method as set forth in claim 2 wherein the bisphosphonate is zoledronate.

4. The method as set forth in claim 1 wherein the carrier is a bone graft material or a bone cement.

5. The method as set forth in claim 4 wherein the bone graft material is a synthetic bone substitute.

6. The method as set forth in claim 5 wherein the synthetic bone substitute comprises tricalcium phosphate and hydroxylapatite.

7. The method as set forth in claim 4 wherein the bone cement comprises hydroxylapatite.

8. The method as set forth in claim 7 wherein the bone cement is a calcium phosphate cement containing hydroxyapatite.

9. The method as set forth in claim 1 wherein the device is a screw.

10. The method as set forth in claim 1, wherein the delivery composition is driven about 2 mm to about 8 mm below the surface of the bone.

11. The method as set forth in claim 1, wherein the delivery composition is driven about 2 mm to about 5 mm below the surface of the bone.

12. The method as set forth in claim 1, wherein the delivery composition is in the shape of wafer or cylinder.

13. The method of claim 1 comprising:
   a) combining the bisphosphonate, strontium ranelate, or both with the carrier to form the delivery composition, wherein the delivery composition is in the form of a wafer;
   b) placing the wafer atop a tibial plateau;
   c) placing the impactor atop the wafer; and d) delivering the effective amount of the delivery composition below the surface of the bone by driving the wafer below the surface of the bone with the mechanical force using a hammer to strike the impactor.

14. The method of claim 1 comprising:
a) combining the bisphosphonate, strontium ranelate, or both with the carrier to form the delivery composition, wherein the delivery composition is in the form of a cylinder;
b) preparing a hole in the bone for receipt of a screw and placing the cylinder into the hole;
c) seating the screw into the hole; and
d) inserting the screw below the surface of the bone, thereby crushing the cylinder into particles, pushing the particles below the surface of the bone, and delivering an effective amount of the delivery composition below the surface of the surrounding bone.

15. A method for strengthening a portion of a bone comprising delivering an effective amount of bisphosphonate, strontium ranelate, or both below a recess or surface feature of a portion of a bone by:
a) placing the bisphosphonate, strontium ranelate, or both into the recess or surface feature of the bone, wherein the bisphosphonate, strontium ranelate, or both is in the form of one selected from the group consisting of a solid, particles, and an aggregation of particles;
b) placing an impact device atop the bisphosphonate, strontium ranelate, or both; or seating a fastening device into recess or surface feature atop the bisphosphonate, strontium ranelate, or both; and
c) using the impact device or the fastening device to crush or break the bisphosphonate, strontium ranelate, or both while driving an effective amount of the bisphosphonate, strontium ranelate, or both about 1 mm to about 10 mm below the surface of the bone.

16. The method as set forth in claim 15 wherein the bisphosphonate is selected from the group consisting of alendronate, clodronate, etidronate, ibandronate, neridronate, olpadronate, pamidronate, risedronate, tiludronate, and zoledronate.

17. The method as set forth in claim 16 wherein the bisphosphonate is zoledronate.

18. The method as set forth in claim 15 wherein the device is a screw.

19. The method as set forth in claim 15 wherein the portion of a bone is the portion of a bone adjacent to a bone implant or prosthesis.

* * * * *